US010251698B2

(12) United States Patent
Greifeneder et al.

(10) Patent No.: US 10,251,698 B2
(45) Date of Patent: Apr. 9, 2019

(54) ABLATION CATHETER

(71) Applicant: CathRx Ltd, Homebush Bay, New South Wales (AU)

(72) Inventors: Roman Greifeneder, Bexley (AU); Tyler McKinley Mortimer, Bondi Beach (AU); David Ogle, Cowan (AU)

(73) Assignee: CathRx Ltd, New South Wales (AU)

( * ) Notice: Subject to any disclaimer, the term of this patent is extended or adjusted under 35 U.S.C. 154(b) by 394 days.

(21) Appl. No.: 14/785,532

(22) PCT Filed: Apr. 22, 2014

(86) PCT No.: PCT/AU2014/000457
§ 371 (c)(1),
(2) Date: Oct. 19, 2015

(87) PCT Pub. No.: WO2014/172746
PCT Pub. Date: Oct. 30, 2014

(65) Prior Publication Data
US 2016/0095650 A1    Apr. 7, 2016

(30) Foreign Application Priority Data

Apr. 22, 2013  (AU) ................................ 2013901396

(51) Int. Cl.
*A61B 18/18*    (2006.01)
*A61B 18/14*    (2006.01)
(Continued)

(52) U.S. Cl.
CPC ...... *A61B 18/1492* (2013.01); *A61B 17/3203* (2013.01); *A61N 1/40* (2013.01);
(Continued)

(58) Field of Classification Search
CPC ............ A61B 17/3203; A61B 18/1492; A61B 2017/003; A61B 2017/0046;
(Continued)

(56) References Cited

U.S. PATENT DOCUMENTS 4,967,765 A * 11/1990 Turner ..................... A61B 5/01
600/549
5,782,828 A    7/1998 Chen et al.
(Continued)

FOREIGN PATENT DOCUMENTS

CN    102125725 A    7/2011
CN    102274074 A    12/2011
(Continued)

OTHER PUBLICATIONS

Search Report from International Application No. PCT/AU2014/000457 dated Sep. 1, 2014, 4 pages.
(Continued)

*Primary Examiner* — Michael Peffley
*Assistant Examiner* — Amanda Zink
(74) *Attorney, Agent, or Firm* — TraskBritt

(57) ABSTRACT

An ablation catheter includes a control handle and a catheter sheath removably connectable to the control handle, the catheter sheath defining a fluid lumen and having a plurality of perforations proximal the distal end of the catheter sheath. The ablation catheter further includes a shape-imparting element inserted into the fluid lumen of the catheter sheath and removably connectable to the control handle. The shape-imparting element is connectable to an RF energy source so that, in use, the shape-imparting elements act as an electrode charging fluid into the fluid lumen to be expelled through the plurality of perforations on the catheter sheath.

20 Claims, 4 Drawing Sheets

(51) Int. Cl.
*A61N 1/40* (2006.01)
*A61B 17/3203* (2006.01)
*A61B 17/00* (2006.01)
*A61B 18/00* (2006.01)

(52) U.S. Cl.
CPC . *A61B 2017/003* (2013.01); *A61B 2017/0046* (2013.01); *A61B 2017/00477* (2013.01); *A61B 2018/00029* (2013.01); *A61B 2018/00077* (2013.01); *A61B 2018/00178* (2013.01); *A61B 2018/00196* (2013.01); *A61B 2018/00214* (2013.01); *A61B 2018/00351* (2013.01); *A61B 2018/00577* (2013.01); *A61B 2018/00636* (2013.01); *A61B 2018/00916* (2013.01); *A61B 2018/1407* (2013.01); *A61B 2018/1467* (2013.01); *A61B 2018/1472* (2013.01); *A61B 2218/002* (2013.01)

(58) Field of Classification Search
CPC .... A61B 17/00477; A61B 2018/00029; A61B 2018/00077; A61B 2018/00178; A61B 2018/00196; A61B 2018/00214; A61B 2018/00351; A61B 2018/00577; A61B 2018/00636; A61B 2018/00916
See application file for complete search history.

(56) References Cited

U.S. PATENT DOCUMENTS

| | | | |
|---|---|---|---|
| 2002/0111618 | A1 | 8/2002 | Stewart et al. |
| 2003/0105453 | A1 | 6/2003 | Stewart et al. |
| 2005/0010095 | A1 | 1/2005 | Stewart et al. |
| 2005/0055019 | A1* | 3/2005 | Skarda ............... A61B 18/1492 606/41 |
| 2008/0161790 | A1 | 7/2008 | Dando et al. |
| 2012/0029444 | A1 | 2/2012 | Anderson et al. |

FOREIGN PATENT DOCUMENTS

| | | |
|---|---|---|
| JP | 2008531139 A | 8/2008 |
| JP | 2009504364 A | 2/2009 |
| WO | 2011140586 A1 | 11/2011 |
| WO | 2012088564 A1 | 7/2012 |
| WO | 2013142906 A1 | 10/2013 |

OTHER PUBLICATIONS

Australian Examination Report No. 1 for Australian Application No. 2014256841, dated Aug. 28, 2017, 4 pages.
Australian Examination Report No. 1 for Australian Application No. 2014202179, dated Apr. 8, 2015, 3 pages.
Australian Examination Report No. 2 for Australian Application No. 2014202179, dated Jun. 25, 2015, 4 pages.
Australian Examination Report No. 3 for Australian Application No. 2014202179, dated Aug. 13, 2015, 4 pages.
Australian Examination Report No. 4 for Australian Application No. 2014202179, dated Sep. 15, 2015, 3 pages.
Chinese First Office Action for Chinese Application No. 201480021037.0, dated Feb. 4, 2017, 15 pages with English Translation.
Chinese First Search for Chinese Application No. 201480021037.0, dated Jan. 23, 2017, 1 page.
European Search Report and Opinion for European Application No. EP14787983, dated Oct. 20, 2016, 9 pages.
International Written Opinion for International Application No. PCT/AU2014/000457, dated Sep. 1, 2014, 9 pages.
Japanese Notification of Reasons for Refusal for Japanese Application No. 2016-507957, dated Aug. 29, 2017, 10 pages with English Translation.
Japanese Search Report for Japanese Application No. 2016-507957, dated Aug. 24, 2017, 25 pages with English Translation.
Australian Examination Report No. 4 for Australian Application No. 2014256841, dated Mar. 7, 2018, 4 pages.
Australian Examination Report No. 3 for Australian Application No. 2014256841, dated Jan. 19, 2018, 4 pages.
Australian Examination Report No. 2 for Australian Application No. 2014256841, dated Nov. 3, 2017, 4 pages.

* cited by examiner

ABLATION CATHETER

CROSS-REFERENCE TO RELATED APPLICATIONS

This application is a national phase entry under 35 U.S.C. § 371 of International Patent Application PCT/AU2014/000457, filed Apr. 22, 2014, designating the United States of America and published in English as International Patent Publication WO 2014/172746 A1 on Oct. 30, 2014, which claims the benefit under Article 8 of the Patent Cooperation Treaty and under 35 U.S.C. § 119(e) to Australian Patent Application Serial No. 2013901396, filed Apr. 22, 2013, the disclosure of each of which is hereby incorporated herein in its entirety by this reference.

TECHNICAL FIELD

This disclosure relates, generally, to a method catheter and, more particularly, to an ablation catheter.

BACKGROUND

Any discussion of the prior art throughout the specification should in no way be considered as an admission that such prior art is widely known or forms part of common general knowledge in the field.

In the conduction of Maze-type procedures, an ablation catheter is used to ablate heart tissue to attempt to clear heart arrhythmias. Generally, a dot ablation is made and this is repeated by re-positioning a tip, ablation electrode of an ablation catheter. This is an extremely time-consuming process. In addition, dot ablation may leave gaps in the lesions, which may again require re-positioning and repeating the procedure. If a clinician could limn longer lesions, fewer manipulations would be required. This would reduce the time to conduct the procedure, which would be beneficial for all concerned. Longer electrodes and multiple electrodes have been considered for radiofrequency ablation but coagulum tends to form on the electrodes. In addition, the energy field from long electrodes is not always uniform and this may cause discontinuities in the lesion. Furthermore, the temperature of the ablation electrodes, as well as the tissue being treated, needs to be carefully maintained to ensure that it does not result in excessive ablation of the tissue.

BRIEF SUMMARY

It is an object of the present invention to overcome or ameliorate at least one of the disadvantages of the prior art, or to provide a useful alternative.

In an aspect, there is provided an ablation catheter that includes a control handle having an electrical connector arranged at a proximal end of the control handle, the electrical connector being connectable to an RF energy source. The catheter further includes a catheter sheath having a proximal end and a distal end, the catheter sheath defining a fluid lumen and having one or more perforations proximal the distal end of the catheter sheath, the catheter sheath being connected to the control handle. The ablation catheter further includes an elongate shape-imparting element of conductive material inserted into the fluid lumen of the catheter sheath and connected to the control handle at an attachment point, and an electrical conductor extending from the electrical connector to the attachment point for electrically connecting the shape-imparting element to the electrical connector.

In one embodiment, the catheter sheath is connected to the control handle via a catheter sheath connector.

In another embodiment, the ablation catheter includes a coupling mechanism for removably connecting the shape-imparting element to the control handle.

In a further embodiment, the ablation catheter includes a fastener for connecting the electrical conductor to the coupling mechanism.

In a yet further embodiment, the ablation catheter includes a fluid tube in a sealing connection with the fluid lumen of the catheter sheath, the fluid tube extending from a catheter sheath connector through the control handle and the proximal end of the control handle to a fluid connector for supplying fluid to the fluid lumen of the catheter sheath.

In another embodiment, the ablation catheter includes a catheter sheath connector for connecting the catheter sheath to the control handle, the catheter sheath extending through the catheter sheath connector and the control handle to the proximal end of the control handle, and being connected to a fluid connector.

In one embodiment, the catheter sheath is removably connectable to the control handle via a catheter sheath connector.

In another embodiment, the shape-imparting element is removably attached to the control handle.

In a further embodiment, the catheter sheath includes conductors embedded within the wall of the sheath.

In a yet further embodiment, the catheter sheath includes at least one sensing electrode.

In another embodiment, the catheter sheath connector includes an electrical sheath connector for connecting conductors from the sensing electrodes to a monitoring device.

In yet a further embodiment, the ablation catheter includes electrical connector elements extending through the control handle to electrically connect the electrical sheath connector to the electrical connector so as to allow the catheter to be connected to the monitoring device.

In another embodiment, the sensing electrodes are positioned adjacent the one or more perforations.

In yet another embodiment, the catheter sheath is formed of a helically wound cable including:
  an inner non-conductive tubular member; and
  an outer layer having a plurality of conductors coiled in a helical manner embedded within the wall of the outer layer.

In one embodiment, a distal portion of the outer layer including the conductors embedded within the wall of that portion of the outer layer is removed to expose a distal portion of the inner non-conductive tubular member, and wherein the perforations are formed on the exposed portion of the inner non-conductive tubular member.

BRIEF DESCRIPTION OF THE DRAWINGS

Preferred embodiments of the disclosure will now be described, by way of example only, with reference to the accompanying drawings in which.

DETAILED DESCRIPTION

Figure 1:
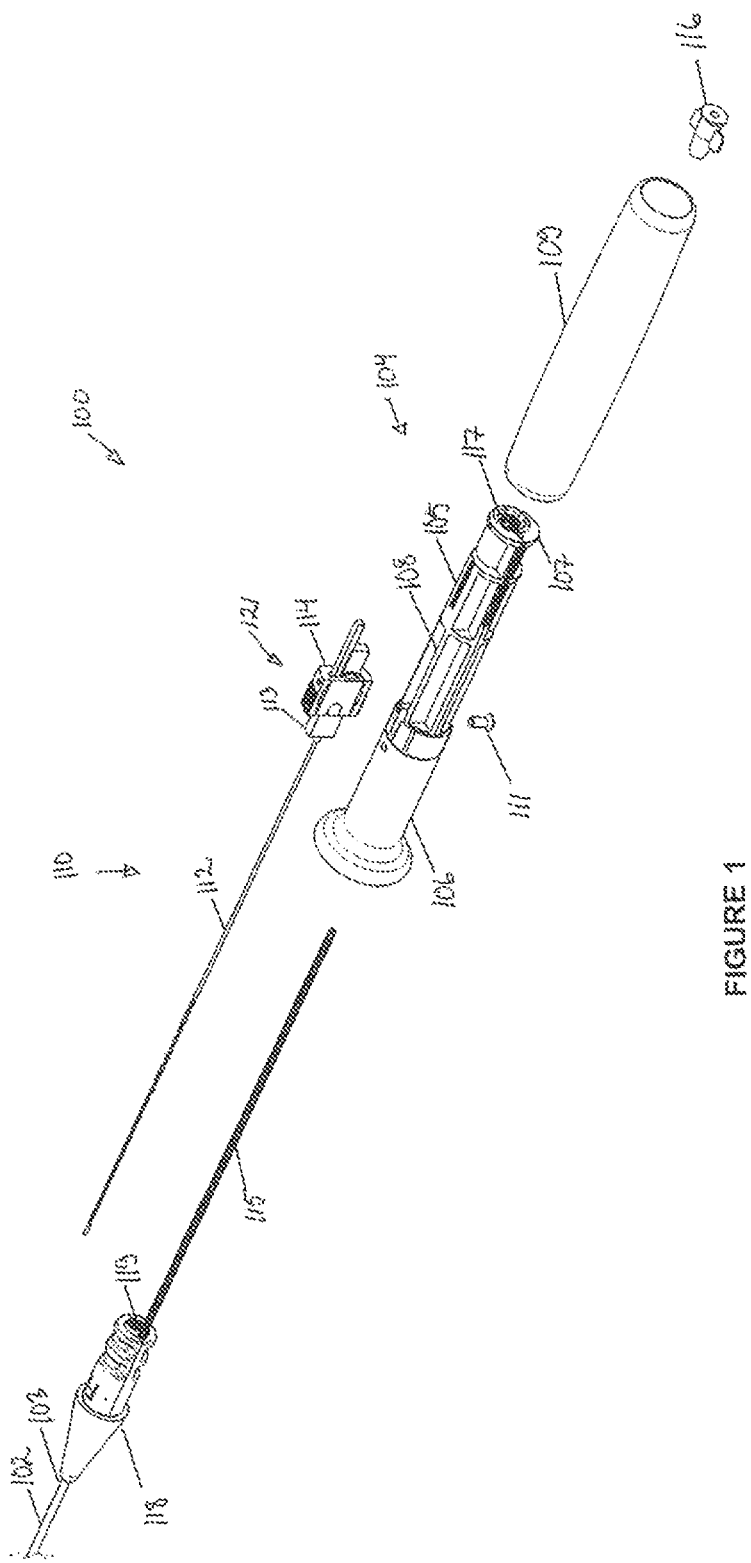
FIG. 1 shows a schematic view of individual elements of a proximal part of an ablation catheter.

FIG. 1 of the drawings shows the individual parts of the proximal end of a modular ablation catheter 100. The individual components are also considered as embodiments of the disclosure. A catheter sheath 102 defines a fluid lumen that extends from a proximal end 103 of the catheter sheath 102 to the distal end of the catheter sheath 102 (not shown in FIG. 1). The catheter sheath 102 is a tubular member made of a suitable polymeric material such as polyethylene or polyether block amide (PEBAX®). Other suitable, biocompatible polymeric materials could also be used. The catheter sheath 102 may also include conductors embedded within the wall of the catheter sheath 102 as explained in reference to FIG. 5 below.

The ablation catheter of FIG. 1 includes a handle assembly 104 including a body 105. The body 105 extends between a distal end 106 and a proximal end 107. The body includes a compartment 108 that is configured to receive a shape-imparting element 110 such as a stylet that can be used to deflect the distal end of the catheter.

Referring to FIG. 1, the catheter sheath 102 connects removably to the body 105 of the handle at its proximal portion 103. The handle assembly 104 also includes a cover 109 removably attachable to the body 105. This attachment may be a slidable connection, a screw, or a screw assembly that allows the attachment of the cover 109 to the body 105.

The shape-imparting element 110 is removably mountable to body 105. Specifically, the shape-imparting element 110 is mounted within compartment 108 defined by the body 105. The body 105 includes an aperture at an attachment point (not shown in FIG. 1) configured to receive a fastener 111 for the removable attachment of the shape-imparting element 110 to the handle.

In one embodiment, the shape-imparting element 110 includes an outer tubular member 112, an inner actuator (not shown in FIG. 1), and a coupling mechanism 121 for removably and releasably coupling the shape-imparting element to the catheter handle. The outer tubular member 112 defines a lumen configured to receive the inner actuator (not shown in FIG. 1). The distal end of the inner actuator, such as a pull wire or the like, is attached to the distal end of the outer tubular member so that the relative movement of the inner actuator and the outer tubular member results in deflection of the distal end of the shape-imparting element.

The coupling mechanism 121 includes a friction block 113 and a slide 114. The outer tubular member 112 is attached to a friction block 113, and the inner actuator is attached to a slide 114. Friction block 113 is configured to receive the fastener 111 such that the outer tubular member of the shape-imparting element 110 is, in use, fixedly mounted to body 105. That is, fastener 111 connects the friction block 113 to the body 105 by attaching to an appropriate aperture (not shown in FIG. 1) in the body 105. It will be appreciated by those skilled in the art that other embodiments of the invention include alternative methods for fixedly mounting the tubular member 112 to body 105, in use. The inner actuator of the shape-imparting element is, in use, movably mounted to body 105 via slide 114. Slide 114 is connected to cover 109 so that pushing the body 105 displaces the handle body 105 and the outer tubular member 112 in relation to cover 109 and thus inner actuator of the shape-imparting element. In use, displacement of the inner actuator or the slide 114 with respect to outer tubular member 112 controls shape-imparting element 110. More specifically, movement of the inner actuator or the slide 114 with respect to the outer tubular member 112, in use, steers or imparts a shape in the distal end of the catheter sheath 102.

In another embodiment, the shape-imparting element 110 includes a shape-imparting stylet received within the lumen of the catheter sheath 102. The stylet is configured to impart a shape in the distal end of the catheter sheath 102. It is also possible for the outer tubular member 112 of the shape-imparting element 110 to have a predetermined non-linear shape, such as a loop or a double loop, which imparts a shape to the distal end of the catheter sheath 102. Various arrangements of steering mechanisms and shape-imparting elements are discussed in other patent applications naming the present applicant, which are herein incorporated by this reference.

It will be appreciated that the terms "releasably connectable," "removably attached," and the like, as used herein, refers to arrangements whereby two components are configured in such a manner so as to enable their connection/attachment, and enable that connection/attachment to be reversed without necessarily damaging either component. That is, the connection/attachment is repeatable. This is significant in the context of a modular device, as the various individual components may be interchanged between devices (for example, where some components are discarded after use) and others reprocessed (e.g., cleaned or otherwise serviced) for further use. It is also to be noted that each one of the shape-imparting elements and the catheter sheath may be fixedly attached to the handle. It is a preferred embodiment that the connection between the handle and the shape-imparting element or the catheter sheath is releasable.

In use, pressurized fluid is supplied to the fluid lumen of the catheter sheath 102 via a fluid connector element 116 and a fluid tube 115. The fluid tube 115 extends inside the handle from the distal part 106 of the handle body 105 through to the proximal part 107 of the handle body 105 and connects to a fluid connector element 116. The fluid connector element 116 is a Luer connector or similar that ensures a sealing connection from the connector element 116 to the fluid tube 115. In an embodiment, the proximal end of the catheter sheath extends through a catheter sheath connector 118 so that the fluid tube 115 consists of the proximal part of the catheter sheath 102.

The catheter sheath connector 118 is arranged on the catheter sheath 102 and includes an electrical connector 119 for connecting conductors from sensing electrodes to a monitoring device, when sensing electrodes are used. This is discussed in more detail below with reference to FIGS. 4*a* and 4*b*. The catheter sheath connector 118 may include any suitable form of electrical connector such as, for example, an electrical plug-type arrangement, a slip-ring type arrangement or the like. When the catheter sheath does not include any sensing electrodes, electrical connector 119 is not needed. The catheter sheath connector 118 further includes a snap-on connector 120 and a complimentary receiving element at the distal end of the handle (not shown in FIG. 1 or 2). The snap-on connector 120 and its complimentary snap-on receiving element on the handle enable the detachable connection of the catheter sheath to the handle.

Figure 2:
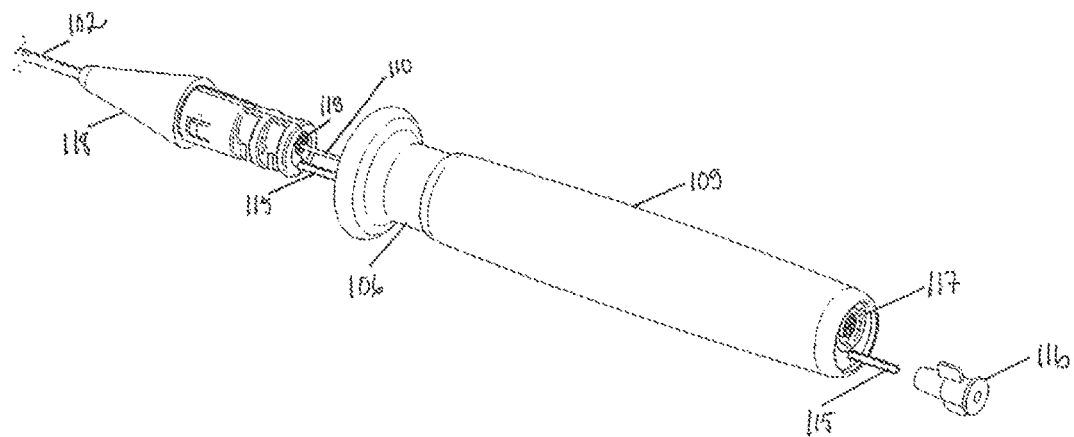
FIG. 2 shows a schematic view of a proximal part of an ablation catheter.

The catheter sheath connector 118, as well as its complimentary part on the handle body, is formed to allow the passage of the shape-imparting element 110 through it as well as the fluid tube. Each connector part includes a bore through which the shape-imparting mechanism and the fluid tube are able to pass. This can be seen in more detail in FIG. 2. In FIG. 2, the catheter sheath connector 118 includes an electrical connector 119 that is modified so that the shape-imparting element 110 can pass through the connectors 119 and 118.

When sensing electrodes are being used, electrical connectors (not shown in FIG. 1 or 2) extend from the complimentary connector element at the distal end 106 of the handle assembly 104 through the handle body 105 to an electrical connector 117 at the proximal end 107 of the handle so as to allow the catheter to be connected to a patient monitor or the like. The electrical connector 117 at the proximal end of the handle also allows a source of ablation energy to be connected to the shape-imparting element 110. The electrical connector 117 preferably incorporates a slip ring arrangement or similar form of rotation permitting arrangement, to allow rotation of the handle without rotating the patient cable.

Ablation of tissue is achieved by energizing fluid supplied to the catheter sheath fluid lumen by RF (radio frequency) energy. The fluid in the fluid lumen of the catheter sheath 102 is energized by supplying the shape-imparting element 110 with RF energy from an RF energy source via the electrical connector 117. A conductor (not shown in FIG. 1 or 2) is connected from the electrical connector 117 to the outer tubular member 112 of the shape-imparting element 110. The conductor wire extends from the electrical connector 117 through the handle body 105 to the attachment point of the shape-imparting element. In the embodiment of FIG. 1, the attachment point is the point where the fastener 111 attaches the shape-imparting element to the handle. At the attachment point, the conductor wire is attached to the electrically conductive coupling mechanism 121, which then conducts the RF energy to the outer tubular member 112 thereby to charge the shape-imparting element 110 with the RF energy. The connection between the conductor and coupling mechanism 121 can be implemented so that the conductor is pressed against the friction block 113 by fastener 111. The charged shape-imparting element 110 energizes the fluid adjacent the shape-imparting element in the fluid lumen and the energized and pressurized fluid is then expelled to the tissue through one or more perforations at the distal end of the catheter sheath 102. The shape-imparting element 110 thus also acts as an electrode and no separate electrode is needed for charging the fluid with RF energy.

Ablation catheters accordingly to embodiments of the invention are thus simpler in structure as there is no need for a separate electrode for charging the fluid with RF energy. This simplified structure is advantageous from a manufacturing and cost perspective.

Figure 3:
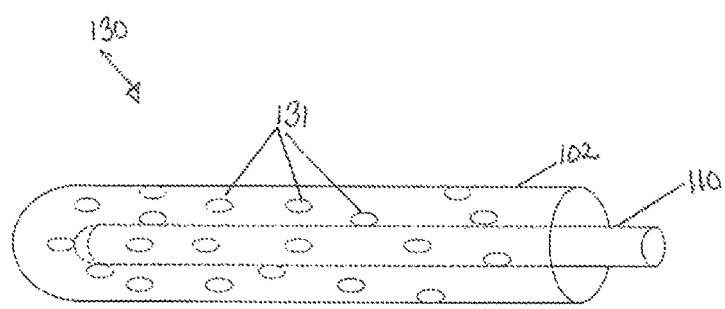
FIG. 3 shows a schematic side view of a distal end of an ablation catheter.

FIG. 3 depicts a distal end 130 of the catheter sheath 102. Ablation of tissue is achieved by RF (radio frequency) energy transfer through conductive saline fluid escaping the distal end 130 of the catheter sheath through multiple perforations 131. These perforations 131 may populate the entire wall of the catheter sheath 102 or they may be arranged at a pre-determined formation on the sheath so as to direct the fluid path to a desired location. The fluid is supplied to the fluid lumen of the catheter sheath by an irrigation pump via the connector element 116 and the fluid tube 115. The fluid is energized by the adjacent shape-imparting element 110, which is charged with the RF energy. The energized and pressurized fluid is expelled toward the tissue through the multiple perforations 131 in the distal end 130 of the catheter sheath 102.

Figure 4A:
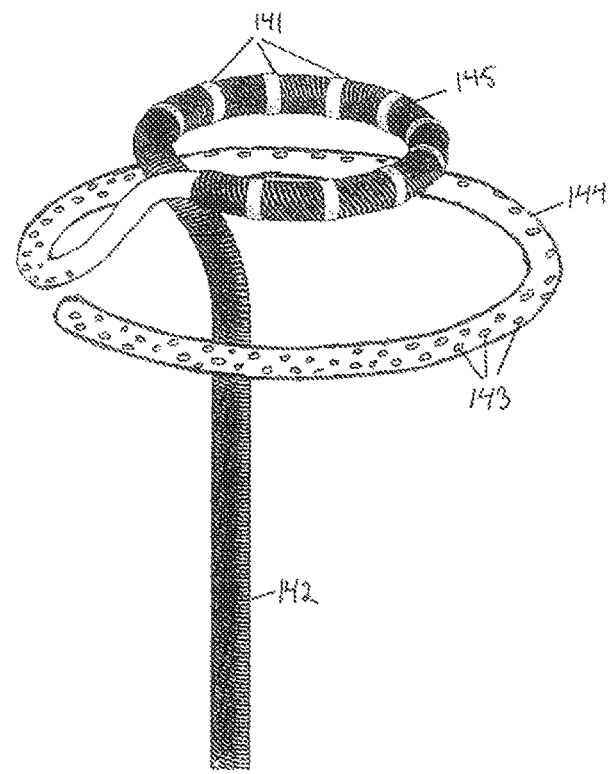
FIGS. 4a and 4b show a distal end of an ablation catheter having a double loop at the distal end.
Figure 4B:
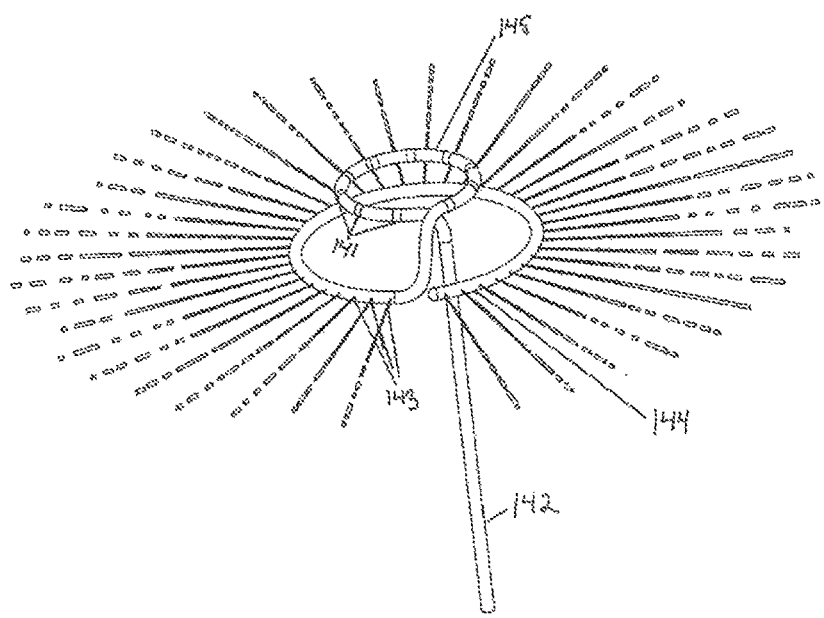

The distal end of the ablation catheter may be of straight configuration as seen in FIG. 3. It is also possible that the distal end of the shape-imparting element is made of a shape-memory wire. As the shape-imparting element is inserted into the fluid lumen of the catheter sheath, it will impart a desired shape to the distal end of the catheter sheath. The distal end of the catheter sheath may also be heat set to a loop shape. The size of the loop may also be variable. FIGS. 4a and 4b show a double loop catheter having a first, smaller loop with sensing electrodes on the catheter sheath and a second, larger loop with perforations arranged around the catheter sheath. In the embodiment depicted in FIG. 3, the perforations are located evenly around the distal end of the catheter sheath. However, any pattern of the perforations can be used. In a loop embodiment such as shown in FIGS. 4a and 4b, for example, covering one-third of the surface of the sheath is used, preferably the outer surface of the loop. Using directional RF energy by different directional patterns of the perforations means that lower power levels will be required to create an effective lesion as less energy is lost to the blood pool.

Figure 5:
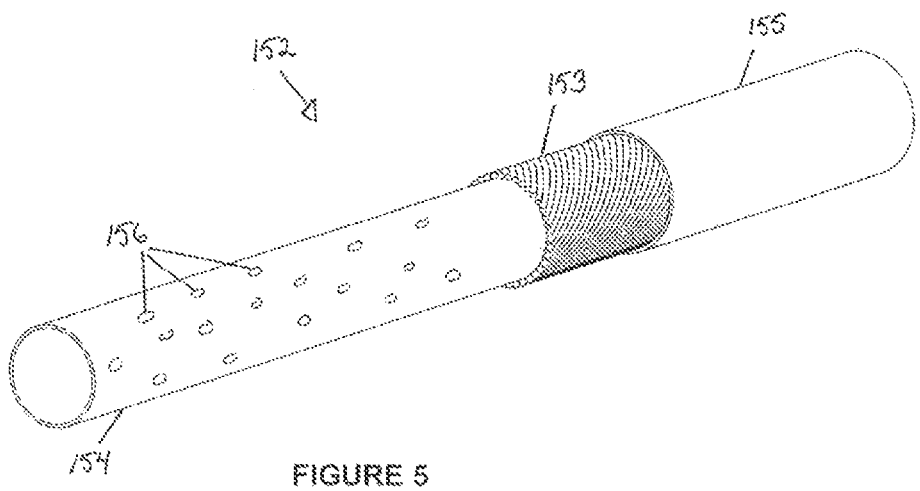
FIG. 5 shows a cable used for making a catheter sheath.

With reference to FIG. 5, a catheter sheath is described that can be used for a double loop catheter shown in FIGS. 4a and 4b. The catheter sheath may be made of a helically wound cable 152. A plurality of conductors 153 are coiled in a helical manner around the outer surface of an inner non-conductive tubular member 154. The cable 152 also includes an outer polymeric layer 155 on top of the conductors so as to form a cable having a layer of helically wound conductors embedded within a wall of the cable. This allows for the sensing electrodes to be formed on the surface of the tubular element in any desired pattern. In addition, it allows for a large number of sensing electrodes to be formed on the tubular element as there will be no conductors running through the lumen of the tubular element of the catheter. A part of the outer polymeric layer 155 and the conductors 153 are removed by laser cutting. Perforations 156 are formed on the remaining inner non-conductive tubular member 154 so as to create a distal tip of the electrode sheath as shown in FIGS. 4a and 4b.

FIGS. 4a and 4b show the distal tip of an ablation catheter 101 where multiple sensing electrodes 141 are formed on a smaller sensing loop 145, and a larger ablating loop 144 has multiple perforations 143 used for ablating the tissue. The catheter sheath 142 is made of the tubular cable having conductors wound helically between two layers of polymeric material. The sensing loop 145 has sensing electrodes 141 that are formed on the cable by exposing a desired conductor wire by laser cutting and then forming a ring electrode in electrical connection with the exposed conductor wire. The larger ablating loop 144 is made to the distal end of the electrode sheath cable by laser cutting and removing the outer layer and all conductor wires from the length of the circumference of the ablating loop 144. Small perforations 143 are then laser cut on the remaining inner polymeric member. The pattern of the perforations 143 can vary. In FIG. 4a, the perforations are arranged on one-third of the outer surface around the circumference of the ablating loop 144, and in FIG. 4b, they are arranged in a straight line around the outer circumference of the ablating loop 144.

Using irrigation as a conduit for RF energy minimizes edge effects because it virtually increases the size of the electric field source. Edge effects concentrate the RF energy at the edges of the electrodes and cause energy gradients that make the lesion uneven. As there is a constant exchange of irrigation, there is constant cooling at the tissue surface, while continuously delivering energy through the tissue. Charging the shape-imparting element with RF energy simplifies the structure of a catheter as it removes the need for separate ablating electrodes. Irrigation also washes away charred thrombus and other artifacts generated by RF procedures.

Reference throughout this specification to "one embodiment," "some embodiments," or "an embodiment" means that a particular feature, structure or characteristic described in connection with the embodiment is included in at least one embodiment of the present invention. Thus, appearances of the phrases "in one embodiment," "in some embodiments," or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

As used herein, unless otherwise specified, the use of ordinal adjectives "first," "second," "third," etc., to describe a common object, merely indicate that different instances of like objects are referred to, and are not intended to imply that the objects so described must be in a given sequence, either temporally, spatially, in ranking, or in any other manner.

In the claims below and the description herein, any one of the terms "comprising," "comprised of," or "which comprises" is an open term that means including at least the elements/features that follow, but not excluding others. Thus, the term "comprising," when used in the claims, should not be interpreted as being limitative to the means or elements or steps listed thereafter. For example, the scope of the expression "a device comprising A and B" should not be limited to devices consisting only of elements A and B. Any one of the terms "including," or "which includes," or "that includes," as used herein, is also an open term that also means including at least the elements/features that follow the term, but not excluding others. Thus, "including" is synonymous with and means "comprising."

It should be appreciated that in the above description of exemplary embodiments of the disclosure, various features of the disclosure are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this invention.

Furthermore, while some embodiments described herein include some but not other features included in other embodiments, combination of features of different embodiments, as would be understood by those skilled in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Similarly, it is to be noticed that the term "coupled," when used in the claims, should not be interpreted as being limited to direct connections only. The terms "coupled" and "connected," along with their derivatives, may be used. It should be understood that these terms are not intended as synonyms for each other. Thus the scope of the expression "a device A coupled to a device B" should not be limited to devices or systems wherein an output of device A is directly connected to an input of device B. It means that there exists a path between an output of A and an input of B, which may be a path including other devices or means. "Coupled" may mean that two or more elements are either in direct physical or electrical contact, or that two or more elements are not in direct contact with each other but yet still cooperate or interact with each other.

Thus, while there has been described what are believed to be the preferred embodiments of the invention, those skilled in the art will recognize that other and further modifications may be made thereto without departing from the spirit of the invention, and it is intended to claim all such changes and modifications as falling within the scope of the invention. For example, any formulas given above are merely representative of procedures that may be used. Functionality may be added or deleted from the block diagrams and operations may be interchanged among functional blocks. Steps may be added or deleted to methods described within the scope of the invention.

It will be appreciated by persons skilled in the art that numerous variations and/or modifications may be made to the disclosure as shown in the specific embodiments without departing from the scope of the disclosure as broadly described. The present embodiments are, therefore, to be considered in all respects as illustrative and not restrictive.

The invention claimed is:

1. An ablation catheter comprising:
   a control handle having an electrical connector arranged at a proximal end of the control handle, the electrical connector being connectable to an RF energy source;
   a catheter sheath having a proximal end and a distal end, the catheter sheath defining a fluid lumen and having one or more perforations proximal the distal end of the catheter sheath, the catheter sheath being connectable to the control handle;
   an elongate shape-imparting element of conductive material inserted into the fluid lumen of the catheter sheath and connected to the control handle at an attachment point; and
   an electrical conductor extending from the electrical connector to the attachment point for electrically connecting the shape-imparting element to the electrical connector and the RF energy source.

2. The ablation catheter of claim 1, further comprising a coupling mechanism for removably connecting the shape-imparting element to the control handle.

3. The ablation catheter of claim 2, further comprising a fastener for connecting the electrical conductor to the coupling mechanism.

4. The ablation catheter of claim 3, wherein the catheter sheath includes a catheter sheath connector for connecting the catheter sheath to the control handle, the catheter sheath extending through the catheter sheath connector and the control handle to the proximal end of the control handle, and being connected to a fluid connector.

5. The ablation catheter of claim 4, wherein the catheter sheath is removably connectable to the control handle via a catheter sheath connector.

6. The ablation catheter of claim 5, wherein the shape-imparting element is removably attached to the control handle.

7. The ablation catheter of claim 6, wherein the catheter sheath includes conductors embedded within the wall of the sheath.

8. The ablation catheter of claim 7, wherein the catheter sheath includes at least one sensing electrode.

9. The ablation catheter of claim 8, wherein the catheter sheath connector includes an electrical sheath connector for connecting conductors from the sensing electrodes to a monitoring device.

10. The ablation catheter of claim 9, further comprising electrical connector elements extending through the control handle to electrically connect the electrical sheath connector to the electrical connector so as to allow the catheter to be connected to the monitoring device.

11. The ablation catheter of claim 10, wherein the sensing electrodes are positioned adjacent the one or more perforations.

12. The ablation catheter of claim 10, wherein the catheter sheath is formed of a helically wound cable including:
- an inner non-conductive tubular member; and
- an outer layer having a plurality of conductors coiled in a helical manner embedded within the wall of the outer layer.

13. The ablation catheter of claim 12, wherein a distal portion of the outer layer including the conductors embedded within the wall of that portion of the outer layer is removed to expose a distal portion of the inner non-conductive tubular member, and wherein the perforations are formed on the exposed portion of the inner non-conductive tubular member.

14. The ablation catheter of claim 3, further comprising a fluid tube in a sealing connection with the fluid lumen of the catheter sheath, the fluid tube extending from a catheter sheath connector through the control handle and the proximal end of the control handle to a fluid connector for supplying fluid to the fluid lumen of the catheter sheath.

15. The ablation catheter of claim 14, wherein the catheter sheath includes a catheter sheath connector for connecting the catheter sheath to the control handle, the catheter sheath extending through the catheter sheath connector and the control handle to the proximal end of the control handle, and being connected to a fluid connector.

16. The ablation catheter of claim 15, wherein the catheter sheath is removably connectable to the control handle via a catheter sheath connector.

17. The ablation catheter of claim 16, wherein the shape-imparting element is removably attached to the control handle.

18. The ablation catheter of claim 17, wherein the catheter sheath includes conductors embedded within the wall of the sheath.

19. The ablation catheter of claim 18, wherein the catheter sheath includes at least one sensing electrode.

20. The ablation catheter of claim 19, wherein the catheter sheath connector includes an electrical sheath connector for connecting conductors from the sensing electrodes to a monitoring device.

* * * * *

UNITED STATES PATENT AND TRADEMARK OFFICE
CERTIFICATE OF CORRECTION

PATENT NO. : 10,251,698 B2
APPLICATION NO. : 14/785532
DATED : April 9, 2019
INVENTOR(S) : Roman Greifeneder et al.

It is certified that error appears in the above-identified patent and that said Letters Patent is hereby corrected as shown below:

In the Specification
Column 1, Line 35, change "could limn longer" to --could form longer--

Signed and Sealed this
Twenty-first Day of May, 2019

Andrei Iancu
*Director of the United States Patent and Trademark Office*